U.S. Patent Number: 5,466,867
Date of Patent: Nov. 14, 1995

United States Patent [19]
Lin et al.

[54] METHOD FOR PRODUCING [S,S]-ETHYLENEDIAMINE-N,N'-DISUCCINIC ACID FROM ITS CALCIUM SALT

[75] Inventors: Ronny W. Lin, Baton Rouge; Eldon E. Atkinson, Jr., Greenwell Springs; William J. Layman, Jr., Baton Rouge, all of La.

[73] Assignee: Albemarle Corporation, Richmond, Va.

[21] Appl. No.: 272,469

[22] Filed: Jul. 11, 1994

[51] Int. Cl.$^6$ .................... C07C 227/18; C07C 227/28; C07C 229/06
[52] U.S. Cl. ............................................ 562/554; 562/565
[58] Field of Search ...................... 562/554, 565

[56] References Cited

U.S. PATENT DOCUMENTS

| | | | |
|---|---|---|---|
| 2,564,092 | 8/1951 | Bersworth | 562/565 |
| 3,077,487 | 2/1963 | Ramsey et al. | 562/565 |
| 3,158,635 | 11/1964 | Kezerian et al. | 562/565 X |
| 4,299,978 | 11/1981 | Nakayasu et al. | 562/554 |
| 4,704,233 | 11/1987 | Hartman et al. | 252/527 |

OTHER PUBLICATIONS

Neal, et al., "Stereospecific Ligands and Their Complexes. I. A. Cobalt(III) Complex of Ethylenediaminedisuccinic Acid", *Journal of Inorganic Chemistry*, vol. 7, No. 11, Nov., 1958, pp. 2405–2412.

*Primary Examiner*—Floyd D. Higel
*Attorney, Agent, or Firm*—E. E. Spielman, Jr.

[57] ABSTRACT

This invention relates to a method for converting calcium salts of [S,S]-ethylenediamine-N,N'-disuccinic acid to an easily filterable precipitate of [S,S]-ethylenediamine-N,N'-disuccinic acid.

16 Claims, No Drawings

5,466,867

METHOD FOR PRODUCING [S,S]-ETHYLENEDIAMINE-N,N'-DISUCCINIC ACID FROM ITS CALCIUM SALT

BACKGROUND OF THE INVENTION

This invention relates to a method for converting the calcium salts of [S,S]-ethylenediamine-N,N'-disuccinic acid to a filterable or centrifugable precipitate of the corresponding acid.

Ethylenediamine-N,N'-disuccinic acid (EDDS) and its various alkali metal, alkaline earth metal, ammonium and substituted ammonium salts are well recognized by the detergent industry as useful chelating agents in cleaning formulations. (See U.S. Pat. No. 4,704,233, which is incorporated herein by reference as if fully set forth.) These salts and acids are theorized to chelate metals such as iron, manganese, copper and other multivalent metal ions. The metal ions are constituents of certain organic stains or act to stabilize such stains when present in washing solutions. Besides providing for the chelating function, EDDS and its salts are non-phosphorous compounds and, as a result, are environmentally desirable. Even further, EDDS and its salts exhibit biodegradability. The degree of biodegradability depends upon the optical EDDS isomer involved. Of the three optical isomers, [R,R], [R,S] and [S,S], the [S,S] isomer is most easily biodegradable and is thus preferred.

The [S,S] isomer can be synthesized from L-aspartic acid and 1,2-dibromoethane. A particularly attractive route features reacting the aspartic acid, as sodium L-aspartate, with 1,2-dibromoethane in a basic aqueous medium to yield, in solution, the sodium salts of [S,S] EDDS. See Neal and Rose, Stereospecific Ligands and Their Complexes of Ethylenediamine-disuccinic Acid, *Inorganic Chemistry*, Vol. 7. (1968), pp. 2405–2412. According to Neal and Rose, the EDDS can be recovered from the solution by slow acidification with concentrated hydrochloric acid to obtain a solution pH of 3.5. The acidification converts the [S,S] EDDS salt to its acid, which acid crystallizes and precipitates from the solution. Fine crystals are said to precipitate out as the pH moves between pH 7 and 3.5. To purify the EDDS precipitate, which is contaminated with co-precipitates, the solids are recovered and redissolved in a NaOH solution followed by reacidification. The cycle is repeated two times. The final precipitate is washed with water to remove HCl and any traces of L-aspartic acid. While it is implied by Neal and Rose that this purification procedure yields a pure product, the procedure is burdened in terms of procedure time and in terms of HCl utilization due to the multi-cycle purification train.

It has been proposed that the drawbacks of Neal and Rose can be significantly reduced by forming the calcium salt of [S,S] EDDS rather than the sodium salt. The calcium salt is formed by the reaction of calcium aspartate with 1,2-dibromoethane in a basic aqueous solution. The calcium salt has low solubility at a high pH, say from 9.5 to 11, and thus, can be easily precipitated from the aqueous solution. There is little contamination from the co-precipitation of the L-aspartic acid salt as this salt is essentially soluble in the high basic aqueous solution. Thus, there is no need for the acidification and redissolution cycle of Neal and Rose. The calcium salt can be recovered from the aqueous solution by filtration or centrifugation.

While the use of the calcium salt avoids the drawbacks of the Neat and Rose process, it is not a panacea. The detergent industry prefers to not use the calcium salt since the calcium cation is associated with water hardness. Instead, it is preferred to use the [S,S] EDDS acid itself or its sodium salts. The art would anticipate that the conversion of the calcium salt to the acid would be a simple matter of acidifying the salt with a mineral acid by adding the mineral acid to an aqueous slurry containing the calcium salt precipitate. The resultant reaction mix would be predicted to comprise a filterable [S,S] EDDS precipitate and an aqueous solution of by-product and other salts. With this anticipated simple conversion, the calcium salt would maintain its advantage over the Neal and Rose sodium salt route. Unfortunately, this simple procedure does not form the expected filterable acid precipitate, but rather, forms a solid mass or very thick slurry. This formation is seen soon after the initial addition of the mineral acid. On a commercial scale, the solid or slurry is not practically processable to obtain [S,S] EDDS.

The Invention

This invention features a method for convening calcium [S,S] EDDS salts to an easily filterable/centrifugable [S,S] EDDS precipitate.

More particularly, the method of this invention effects the above conversion by co-feeding, to a volume of water, calcium EDDS salt and an aqueous mineral acid, in which the mineral acid has a dissociation constant within the range of from about $1.0 \times 10^{-5}$ to about $1.0 \times 10^{10}$, wherein the feed rates of the calcium salt and the aqueous mineral acid are controlled so that the volume of water has a pH within the range of from about 1.4 to about 7 at least substantially throughout the co-feed period. It is preferred that the pH be within the range of from about 1.6 to about 6.8 and most highly preferred that the pH lie within the range of from about 3 to about 6.6 during the co-feeding. Further benefit can be obtained when using the most highly preferred range by further reducing the pH to be within the range of from about 1.8 to about 2.4 after the co-feeding is finished. This most highly preferred technique obtains a near quantitative recovery of very pure [S,S] EDDS. The phrase "substantially throughout the co-feed period" is used since there may be an adjustment period or other period in which the pH may not be within the selected range. However, that period will be very short and be measured in seconds, say 1 to 100 seconds, and should not amount to more than 30% of the co-feed period.

The practice of this invention results in the precipitation of [S,S] EDDS from the volume of water, which precipitate can be easily recovered by conventional liquid-solid separation techniques, e.g., filtration, centrifugation and the like. The practice of this invention results in the conversion of almost all, say 95 %, of the calcium [S,S] EDDS salt to the [S,S] EDDS precipitate. The precipitate may contain trace amounts of calcium ion which can be reduced by water washing.

The calcium [S,S] EDDS is preferably fed as small particulate or powder to facilitate its reaction with the mineral acid. It is preferred to feed the salt as an aqueous slurry. The amount of water in the slurry can be any convenient amount which facilitates the calcium salt's transport to and mixing in the volume of water. Generally, the water will comprise from about 60 wt % to about 98 wt % of the aqueous slurry, with all or nearly all of the balance being the calcium [S,S] EDDS salt. Since the calcium salt has some solubility in water, say 1 wt %, the liquid portion of the slurry will be basic. Generally, the slurry pH will be within the range of from about 8 to about 11. Most preferably, the pH will be within the range of from about 8.5 to about 9.5.

The aqueous mineral acid used to reduce the pH of volume of water, be it during co-feed or afterwards, will be comprised of a mineral acid having a dissociation constant not lower than about $1.0 \times 10^{-5}$ but not higher than about $1.0 \times 10^{10}$. Many mineral acids can be chosen, e.g., hydrohaloic acids, sulfuric acid, and phosphoric acid. Hydrohaloic acids are preferred, with hydrochloric acid being most preferred. Preferred aqueous hydrochloric acid solutions are the concentrated solutions and more preferably, those solutions which contain 2 to 40 wt % HCl. Most highly preferred are those containing from about 5 to about 37 wt % HCl.

The volume of water to which the aqueous slurry and the aqueous mineral acid are fed serves many purposes. It acts as a mixing medium to effect the efficient mixing of the two feeds. Also, the volume of water acts as a crystallization medium which dilutes the two feeds and effects controlled precipitation of the [S,S] EDDS. Without dilution, supersaturation is possible. The volume of water also provides sufficient volume to dissipate the heat of neutralization. Even further, the volume of water provides sufficient water to hold co-product salts of neutralization, e.g., $CaCl_2$, in solution. For the purposes of this invention, the term "volume of water" means that water volume which is suitable to accomplish the above recited functions during the feeding period or the period during which precipitation occurs.

All of the functions require that the volume of water have a sufficient size. Its size, i.e., volume, will increase over time as the aqueous mineral acid solution and the optional aqueous slurry both contribute water to the volume of water. Thus, with the volume of water ever increasing in size, the sufficiency of the water volume should only be of concern at the initiation of the feeds. The determination of a suitable initial water volume is best made empirically with the goal being the accomplishment of the above-recited functions. The empirical determination should consider the pH of each of the feeds, the salt and acid concentrations of the feeds, the volume feed rate for each of the feeds, and the precipitate quality desired. Generally speaking, the initial volume of water will provide a ratio of the water volume initially present before co-feed to the total water volume added by the two feeds which lies within the range of from about 1:0.1 to about 1:5 and most preferably within the range of from about 1:0.2 to about 1:2.50. The size of the volume of water at any point during the co-feed period will be determined by the sum of the initial size of the volume of water and the amount of water introduced by the two feeds minus any water losses from the reaction system.

It is to be understood that the volume of water will contain various solutes, e.g., L-aspartic acid, inorganic salts and small amount of [S,S] EDDS. The identities and the concentrations of the solutes will most likely change during the co-feed period. The [S,S] EDDS concentration will not increase dramatically as most all of the [S,S] EDDS produced will precipitate out of solution.

It is preferred that the volume of water have an essentially neutral or preacidified pH, i.e., one within the range of from about 4 to about 7, before the feeding begins.

By the term "co-feed" it is meant that the feeds of the calcium salt and the aqueous mineral acid occur substantially together timewise or in alternate portions. When fed together, it is not a deviation from the method of this invention to start or finish one feed somewhat before or after the other, or to have one feed interrupted for a short period of time while the other continues, provided that the pH of the volume of water stays within the prescribed range for the prescribed period of time.

When fed together, the rate of feed for each feed is adjusted in response to maintaining the pH of the volume of water at the desired level. If the water volume becomes too basic, then the mineral acid solution feed rate is increased or the calcium salt feed rate is decreased. The reverse is true if the volume of water becomes too acidic.

The alternating feed technique features the intermittent addition of a portion of one of the feeds and then a portion of the other feed, with attention given to obtaining and maintaining the prescribed acidic pH substantially throughout the period. For example, a portion of the aqueous mineral acid is added until the prescribed water volume pH is obtained. Then a portion of the aqueous calcium salt slurry is added with care being taken to not leave the pH range. Another portion of the aqueous mineral acid is then added followed by another portion of the salt. The sequence is repeated until all of the acid and salt have been added.

The pH adjustments are made by measuring the pH of the water volume and, from these measurements, determining what adjustment, if any, is needed to obtain the desired pH. The pH values recited for the methods of this invention are obtained by the use of conventional pH meters with their probes located in the water volume.

The method of this invention best occurs at any temperature at which the feeds or the volume of water do not boil or freeze. It is preferred that the process pressure be around ambient pressure. The temperature is preferably within the range of from about 5° to about 55° C. Room temperatures and pressures are suitable.

In its broadest definition, the method of this invention accomplishes the conversion of the calcium salt of [S,S] EDDS to an easily filterable/centrifugable precipitate of [S,S] EDDS by exposing the calcium salt, in a volume of water, to a pH which is below 7 throughout substantially all of the period during which a precipitate is being formed in the volume of water.

It is theorized, though the method of this invention is not to be limited by any such theory, that when the aqueous mineral acid is added in the conventional manner, that is, directly to an aqueous slurry of the calcium succinate, the pH of the resultant slurry drops relatively slowly. Such a slow drop allows time for the formation of precipitates of various calcium salts which are not soluble at these declining pH's. This precipitation occurs before the obtainment of the very acidic pH ranges described for the method of this invention and thus, leads to the formation of the before-mentioned solid masses or thick slurries instead of the filterable [S,S] EDDS precipitate which is obtained at the much lower pH values. Instead of a slowly obtained acidic pH, the method of this invention seeks to obtain the desired very acidic pH range in time to substantially concur with the earliest formation of a [S,S] EDDS precipitate. With such timing, the desired precipitate is obtained.

After the acid and salt have been fed, the [S,S] EDDS precipitate is easily recovered from the volume of water by filtration or centrifugation. After the recovery, the [S,S] EDDS precipitate is preferably washed with water. The washed [S,S] EDDS precipitate is essentially pure, preferably containing less that about 0.5 wt % impurities.

The following Examples are meant to illustrate the methods of this invention and are not to be taken as limiting the scope thereof.

EXAMPLE I (Comparative)

617 g of [S,S] EDDS calcium wet cake (0.91 wt % L-aspartic acid and 30.92 wt % [S,S] EDDS) and 640 g of water were charged in a 5-liter flask to make a slurry. 103 g of aqueous 18.5 wt % HCl were added with good agitation for 20 minutes at 21.5°–23.5° C. During the addition, the slurry was first diluted but then quickly solidified in the reactor at pH ~7.26 measured with a re-calibrated pH meter. 1125 g of water were added and the solid cake could not be broken with the agitation. An external or additional mechanical means was needed to reslurry the mixture. Adding 59 g more of 18.5 wt % HCl for 10 minutes to pH 6.94 resulted in a thick slurry (near about re-solidification stage). Addition of 510 g water did not help much. 270 g of 23 wt % HCl were added in <5 minutes to quickly reduce the pH to 2.61 (2.00 after 5-minute additional stirring) to obtain a light slurry at 30.4° C. 10 g of 18.5 wt % HCl were added to obtain a pH 1.88. The pH was 1.96 at 23.4° C. after 175-minute additional stirring. After filtration and wash with 500 g of deionized water, 525 g of wet cake were obtained with 0.13 wt % L-aspartic acid, 39.04 wt % [S,S,]-EDDS, 557 ppm Ca ion, and <0.01 wt % of bromide or chloride. (The filtrate (2704 g) and wash (558 g) were 0.19 and 0.12 wt % L-aspartic acid and 0.02 wt % [S,S] EDDS, respectively.)

The following examples are of this invention.

EXAMPLE II 595 g of [S,S] EDDS calcium wet cake (1.59 wt % L-aspartic acid and 30.11 wt % [S,S] EDDS) in 322 g water slurry were alternatively added with 140 g of 18.5 wt % HCl to 525 g water in a flask in 1.1 hours at a pH range of 4.05–6.38 at ~25° C. to obtain a good slurry. 200 g of water were used to wash the slurry beaker and then added to the reactor. Additional 278 g of 18.5 wt % HCl were added in 47 minutes to reduce pH from 6.38 to 1.89, followed by 0.5 hour additional stir. The slurry was very easily filtered (in ~5 minutes) and the wet cake was washed with 522 g deionized water. The wet cake (253 g) had ~0 wt % L-aspartic acid, 65.67 wt % [S,S] EDDS, 1060 ppm Ca ion, and <0.01 wt % bromide or chloride. (0.64 and 0.11 wt % L-aspartic acid and 0.04 and 0.01 wt % [S,S] EDDS were in the filtrate (1724 g) and wash (544 g), respectively.)

EXAMPLE III 357 g of [S,S] EDDS calcium wet cake (1.24 wt % L-aspartic acid and 27.82 wt % [S,S] EDDS) in 245 g water slurry were alternatively added with 58.6 g of 37 wt % HCl to 196 g water in a flask in 55 minutes at pH ~4–6.50 to obtain a slightly thick slurry at 28.2° C. After the co-feed, 68.8 g of 37 wt % HCl were added in 0.5 hour to reduce the pH to 1.82 at 32.8° C. The slurry was stirred for additional 2.7 hours and was then very easily filtered (in ~5 minutes). After washing with 182 g deionized water, 165 g of [S,S] EDDS wet cake were obtained, which had ~0. wt % L-aspartic acid, 57.88 wt % [S,S] EDDS, 1242 ppm Ca ion, and <0.01 wt % of bromide or chloride. (The filtrate (0.44 wt % L-aspartic acid and 0.03 wt % [S,S] EDDS) was 740 g, while the wash (0.15 wt % L-aspartic acid and 0.01 wt % [S,S] EDDS) was 196 g.)

What is claimed:

1. A method for converting calcium [S,S]-ethylenediamine-N,N'-disuccinic acid salt to a [S,S]-ethylenediamine-N,N'-disuccinic acid precipitate, the method comprising; co-feeding, to a volume of water, calcium [S,S]-ethylenediamine-N,N'-disuccinic acid salt and aqueous mineral acid, the mineral acid having a dissociation constant within the range of from about $1.0 \times 10^{-5}$ to about $1.0 \times 10^{-10}$, wherein the feed rates of the calcium salt and the aqueous mineral acid are controlled so that the volume of water has a pH within the range of from about 1.4 to about 7 at least substantially throughout the co-feed period.

2. The method of claim 1 wherein the calcium [S,S]-ethylenediamine-N,N'-disuccinic acid salt is fed as an aqueous slurry.

3. The method of claim 1 wherein the mineral acid is a hydrohaloic acid.

4. The method of claim 1 wherein the mineral acid is hydrochloric acid.

5. The method of claim 4 wherein the aqueous hydrochloric acid contains from about 2 to about 40 wt % HCl.

6. The method of claim 1 wherein the volume of water will provide a ratio of the water volume initially present before co-feed to the total volume of water added with the co-feed which lies within the range of from about 1:0.1 to about 1:5.

7. The method of claim 6 wherein the ratio is within the range of from about 1:0.2 to about 1:2.5.

8. The method of claim 1 wherein the pH is within the range of from about 1.6 to about 6.8.

9. A method for converting calcium [S,S]-ethylenediamine-N,N'-disuccinic acid salt to a [S,S]-ethylenediamine-N,N'-disuccinic acid precipitate, the method comprising: co-feeding, to a volume of water, calcium [S,S]-ethylenediamine-N,N'-disuccinic acid salt and aqueous mineral acid, the mineral acid having dissociation constant within the range of from about $1.0 \times 10^{-5}$ to about $1.0 \times 10^{10}$, wherein the feed rates of the calcium salt and the aqueous mineral acid are controlled so that the volume of water has a pH within the range of from about 3 to about 6.6 at least substantially throughout the co-feed period; and, subsequent to the co-feeding period, adding additional aqueous mineral acid to the volume of water to reduce its pH so that it is within the range of from about 1.8 to about 2.4.

10. The method of claim 9 wherein the calcium [S,S]-ethylenediamine-N,N'-disuccinic acid salt is fed as an aqueous slurry.

11. The method of claim 9 wherein the mineral acid is a hydrohaloic acid.

12. The method of claim 9 wherein the mineral acid is hydrochloric acid.

13. The method of claim 12 wherein the aqueous hydrochloric acid contains from about 2 to about 40 wt % HCl.

14. The method of claim 9 wherein the volume of water will provide a ratio of the water volume initially present before co-feed to the total volume of water added with the co-feed which lies within the range of from about 1:0.1 to about 1:5.

15. The method of claim 14 wherein the ratio is within the range of from about 1:0.2 to about 1:2.5.

16. The method of claim 1 wherein the pH is within the range of from about 3 to about 6.6.

* * * * *